US00PP20861P2

(12) United States Plant Patent
de Looff

(10) Patent No.: US PP20,861 P2
(45) Date of Patent: Mar. 23, 2010

(54) *LILIUM* PLANT NAMED 'DOUBLE BEAUTY'
(50) Latin Name: *Lilium hybrida*
Varietal Denomination: Double Beauty

(75) Inventor: Tonny M. de Looff, Kouderkerke (NL)
(73) Assignee: De Leoff Lily Innovation BV., Kouderkerke (NL)

( * ) Notice: Subject to any disclaimer, the term of this patent is extended or adjusted under 35 U.S.C. 154(b) by 0 days.
(21) Appl. No.: 12/317,847
(22) Filed: Dec. 30, 2008
(51) Int. Cl.
*A01H 5/00* (2006.01)
(52) U.S. Cl. ..... Plt./315
(58) Field of Classification Search ..... Plt./315
See application file for complete search history.

*Primary Examiner*—Annette H Para
(74) *Attorney, Agent, or Firm*—Penny J. Aguirre

(57) ABSTRACT

A new cultivar of *Lilium* plant named 'Double Beauty', characterized by its double flowers that are pink in color with petals that have deep pink midribs and white margins and it's flowers that lack functional reproductive organs and pollen.

1 Drawing Sheet

Botanical classification:
*Lilium hybrida.*
Varietal denomination: 'Double Beauty'.

BACKGROUND OF THE INVENTION

The present invention relates to a new and distinct cultivar of *Lilium hybrida* and will be referred to hereafter by its cultivar name, 'Double Beauty'. 'Double Beauty' represents a new Oriental lily, grown for use as a cut flower.

The new cultivar, 'Double Beauty' arose from an ongoing breeding program conducted by the Inventor in a greenhouse in Koudekerke, The Netherlands. 'Double Beauty' was selected in summer of 2002 as a single unique plant that arose from a cross made in summer of 1997 with an unnamed proprietary seedling as the female parent and *Lilium* 'Sorbonne' (U.S. Plant Pat. No. 15,886) as the male parent.

Asexual reproduction of the new cultivar was first accomplished by in vitro propagation under the direction of the Inventor in Heerhugowaard, The Netherlands in 2002. It has been determined that the characteristics of the new cultivar are stable and are reproduced true to type in successive generations.

SUMMARY OF THE INVENTION

The following traits have been repeatedly observed and represent the characteristics of the new cultivar after observing plants grown outdoors in a field for five years in Koudekerke, The Netherlands. These attributes in combination distinguish 'Double Beauty' as unique from all other varieties of Oriental lilies known to the Inventor.

1. 'Double Beauty' exhibits double flowers.
2. 'Double Beauty' exhibits flowers with petals that are pink in color with deep pink midribs with white margins.
3. 'Double Beauty' produces flowers that lack functional reproductive organs and pollen.

'Double Beauty' differs from its female parent plant in having a greater number of petaloids. 'Double Beauty' differs from its male parent, 'Sorbonne' in having double flowers whereas 'Sorbonne' exhibits single flowers. The Inventor is familiar with many commercial cultivars and knows of no other cultivars that are similar in comparison to 'Double Beauty'. 'Double Beauty' can be compared to 'Miss Lucy'

(U.S. Plant Pat. No. 15,916), another double flowering Oriental lily. 'Miss Lucy' differs in having flowers that are lighter pink in color and lacks white margins and dark pink midribs.

BRIEF DESCRIPTION OF THE PHOTOGRAPHS

The plants and plant parts in the photographs were taken of plants of 'Double Beauty' as grown in a nursery bed in a greenhouse for 3 months from a bulb 4.5 cm in diameter (2.5 years in age) in Koudekerke, The Netherlands.

The photograph on the top of the sheet provides a close-up view of a flower and flower buds of 'Double Beauty'.

The photograph on the bottom of the sheet provides a close-up view of a leaf of 'Double Beauty'.

The colors in the photograph may differ slightly from the color values cited in the detailed botanical description, which accurately describe the colors of the new Oriental lily.

DERAILED BOTANICAL DESCRIPTION

The following is a detailed description of plants of 'Double Beauty' as grown in a nursery bed in a greenhouse for 3 months from a bulb 4.5 cm in diameter in Koudekerke, The Netherlands. Plants were grown under natural light with average day temperatures ranging from 150 to 30° C. and average night temperatures ranging from 12° to 17° C. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General description:

*Blooming period.*—June in The Netherlands.

*Plant type.*—Perennial bulb, grown for cut flower production.

*Plant habit.*—Upright.

*Height and spread.*—Average of 90 cm in height and 40 cm in spread.

*Cold hardiness.*—At least to U.S.D.A. Zone 5.

*Heat tolerance.*—At least to 40° C.

*Diseases and pests.*—Not more susceptible than other *Lilium* varieties.

*Root description.*—True bulb, globular in shape with a pointed apex, an average of 4.5 cm in height and 4.4 cm in diameter, N155B in color, surface is scaly and dull.

Growth and propagation:

*Propagation.*—Tissue culture preferred, bulb scales also possible.

*Cropping time to bloom.*—About 2.5 years from a rooted transplant from tissue culture to production of flowering stems suitable for cutting.

*Growth rate.*—Moderate.

Stem description:

*Stem shape.*—Round.

*Stem color.*—144B.

*Stem size.*—Average of 68.4 cm in length, average of 7 mm in diameter.

*Stem surface.*—Moderately glossy, glabrous, covered with a thin waxy layer 145A in color.

*Stem aspect.*—Upright, strong.

*Internode length.*—Average of 1.9 cm.

*No. of harvestable cut flower stems.*—1 per bulb.

Foliage description:

*Leaf shape.*—Lanceolate.

*Leaf division.*—Simple.

*Leaf base.*—Attenuate.

*Leaf apex.*—Acuminate.

*Leaf venation.*—Parallel, color on upper surface is 146C, color on lower surface is 146B.

*Leaf margins.*—Entire.

*Leaf attachment.*—Petiolate.

*Leaf arrangement.*—Alternate.

*Leaf surface.*—Glabrous and smooth on upper and lower surface.

*Leaf color.*—Young and mature upper surface; slightly darker than 137A, young and mature lower surface; 137C.

*Leaf number.*—Average of 36 per stem.

*Leaf size.*—Average of 15.9 cm in length and 4.5 cm in width.

*Petioles.*—Flattened, average of 1.8 cm in length and 6 mm in width, 146D in color on upper surface and 145A in color on lower surface.

*Foliage durability to stress.*—High.

Flower description:

*Inflorescence type.*—Double flowers arranged in simple terminal cyme.

*Inflorescence size.*—Average of 24.5 cm in height and 32.3 cm in width.

*Flower fragrance.*—Strong, sweet.

*Inflorescence longevity.*—Average of 14 days on plant, persistent, 14 days as a cut flower.

*Flower bud description.*—Narrowly ovate in shape, average of 3.4 cm in diameter and 9.5 cm in length, color is 145C with base and stripes of 176B.

*Flower quantity.*—Average of 4 per stem.

*Flower aspect.*—Held outward.

*Flower form.*—Double, rotate.

*Flower size.*—12.1 cm in depth and 22.2 cm in diameter.

*Rate of opening.*—Flowers open with the lowest flowers opening first.

*Pedicels.*—None.

*Peduncles.*—9.4 cm in length and 6 mm in diameter with an average angle to stem of 50°, 147C in color, tinged 197A to 197B, strong strength.

*Petals.*—3, about 12.5 cm in length and 5.6 cm in width, narrowly ovate to lanceolate in shape, curved, margin is entire, apex is rounded, surface is smooth and slightly glossy, arrangement is rotate, color when opening and mature; upper surface ranges from 63B to 63C to 64C with a more vivid central band of N57A, base 143C to 144A, at the base there is an average of 40 glands visible; average of 1 mm in length and N57A in color, color of lower surface of petal opening and mature; 65B to 65C, central band and area near base 166A to 166B, base 147D.

*Petaloids.*—15, about 12.5 cm in length and 4.7 cm width, narrowly ovate to lanceolate in shape, concave, margin is entire, surface is smooth and slightly glossy in appearance, color when opening; 65B to 65C, base and central vein; 166 to 166B, base 147D, color when fully open; ranging from 63B to 63C to 64C with a more vivid central band, N57A, base 134C to 144A, at the base there is an average of 40 glands visible; average of 1 mm in length and N57A in color.

*Calyx form.*—Rotate in form, average of 6. 1 cm in length and 22.2 cm in diameter.

*Sepals.*—3, average of 12.7 cm in length, 5 cm in width, narrow ovate to lanceolate in shape, arrangement is rotate, margin is entire, apex is rounded, base is cuneate, surface is smooth and slightly glossy in appearance, color of upper surface (opening and mature) 63B to 64C with a more vivid central band; N57A and lighter outer margins; 69D, base;143C to 144A. Color of underside of sepal opening and mature 70C, lighter towards the margins, outer margin: 69D, base and central band 176B.

Reproductive organs:

*Gynoecium.*—1, pistil strongly deformed, about 2.8 cm in length, stigma is club shaped and strongly deformed 148D in color, style is about 2.7 cm in length 145A in color, ovary is 145C to 145D in color.

*Androecium.*—No stamens present.

*Seeds.*—None observed.

It is claimed:

1. A new and distinct cultivar of *Lilium* plant named 'Double Beauty' as herein illustrated and described.

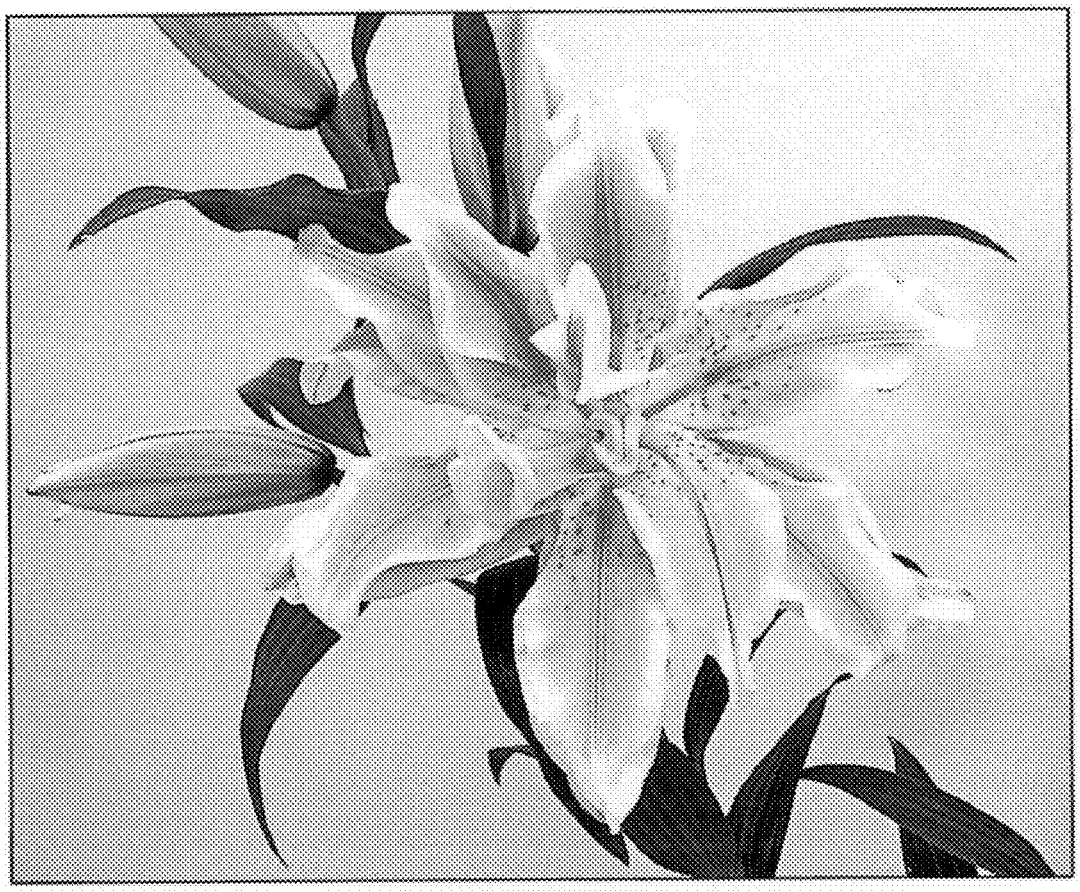
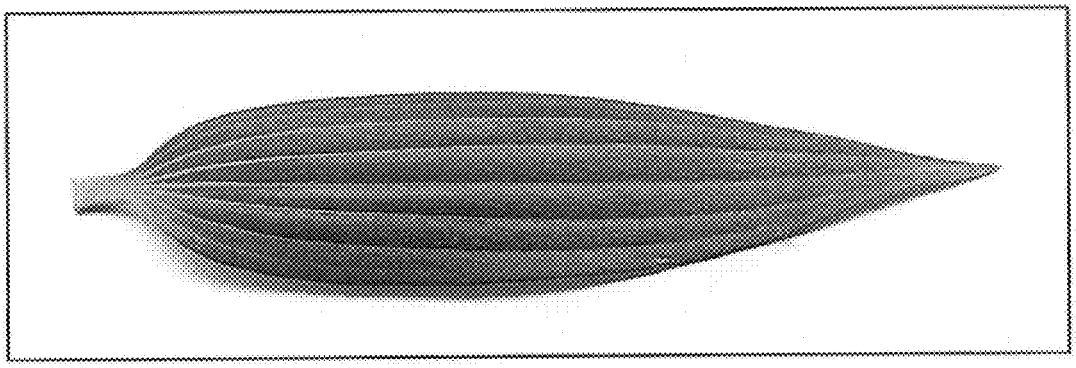

* * * * *